US010357286B2

United States Patent
Petit et al.

(10) Patent No.: US 10,357,286 B2
(45) Date of Patent: Jul. 23, 2019

(54) OSTEOSYNTHESIS SYSTEM COMPRISING MEANS FOR STRAIGHTENING A BONE ANCHORING ELEMENT RELATIVE TO A SCREW HEAD AND ANCHORING SCREW IMPLEMENTED IN SUCH A SYSTEM

(71) Applicant: SAFE ORTHOPAEDICS, Eragny sur Oise (FR)

(72) Inventors: Dominique Petit, Verton (FR); Hervé Vouaillat, Venon (FR); Thomas Droulout, Poissy (FR); Martin Slotwinski, Juziers (FR)

(73) Assignee: SAFE ORTHOPAEDICS, Eragny sur Oise (FR)

(*) Notice: Subject to any disclaimer, the term of this patent is extended or adjusted under 35 U.S.C. 154(b) by 159 days.

(21) Appl. No.: 15/125,361

(22) PCT Filed: Mar. 9, 2015

(86) PCT No.: PCT/FR2015/050576
§ 371 (c)(1),
(2) Date: Sep. 12, 2016

(87) PCT Pub. No.: WO2015/136203
PCT Pub. Date: Sep. 17, 2015

(65) Prior Publication Data
US 2017/0065304 A1    Mar. 9, 2017

(30) Foreign Application Priority Data

Mar. 12, 2014  (FR) ...................................... 14 52045

(51) Int. Cl.
*A61B 17/70*     (2006.01)
*A61B 17/86*     (2006.01)

(52) U.S. Cl.
CPC ...... *A61B 17/7035* (2013.01); *A61B 17/7037* (2013.01); *A61B 17/7079* (2013.01); *A61B 17/8605* (2013.01)

(58) Field of Classification Search
CPC ............ A61B 17/7035; A61B 17/7037; A61B 17/7032
See application file for complete search history.

(56) References Cited

U.S. PATENT DOCUMENTS 6,488,681 B2   12/2002   Martin et al.
6,858,030 B2   2/2005    Martin et al.
(Continued)

FOREIGN PATENT DOCUMENTS

EP    1222899 A2    7/2002
EP    1240875 A1    9/2002
(Continued)

OTHER PUBLICATIONS

International Search Report for PCT/FR/2015/050576 dated Apr. 24, 2015.
(Continued)

*Primary Examiner* — Andrew Yang
(74) *Attorney, Agent, or Firm* — Bachman & LaPointe, P.C.

(57) ABSTRACT

An osteosynthesis system comprising anchoring screws, wherein at least one of the anchoring screws comprises a bone anchoring element with a longitudinal axis AA, comprising a threaded anchoring rod prolonged at the end by a coupling head and a screw head for coupling a connecting element to the bone anchoring element, wherein the screw, comprises a body with a longitudinal axis BB traversed longitudinally by a channel featuring in the lower portion a receiving cavity for receiving the coupling head of the anchoring element, at least one connecting element designed
(Continued)

to interconnect the anchoring screws, means of tightening the connecting element on each anchoring screw, a means of straightening the bone anchoring element in relation to the screw head during tightening, wherein the means of straightening are arranged to straighten the threaded rod of the bone anchoring element and place the former in the longitudinal axis BB.

18 Claims, 5 Drawing Sheets

(56) References Cited

U.S. PATENT DOCUMENTS

| | | | |
|---|---|---|---|
| 7,335,202 | B2 | 2/2008 | Matthis et al. |
| 7,686,834 | B2 | 3/2010 | Saint-Martin |
| 8,167,916 | B2 | 5/2012 | Saint-Martin |
| 8,663,292 | B2 | 3/2014 | Dec et al. |
| 8,845,695 | B2 | 9/2014 | Saint-Martin |
| 8,894,692 | B2 | 11/2014 | Martin et al. |
| 9,339,310 | B2 | 5/2016 | Dec et al. |
| 9,510,862 | B2 | 12/2016 | Montello et al. |
| 2002/0091386 | A1 | 7/2002 | Martin et al. |
| 2002/0133154 | A1 | 9/2002 | Saint-Martin |
| 2002/0183748 | A1 | 12/2002 | Martin et al. |
| 2008/0051794 | A1 | 2/2008 | Dec et al. |
| 2010/0152778 | A1 | 6/2010 | Saint-Martin |
| 2012/0071932 | A1 | 3/2012 | Martin et al. |
| 2012/0179206 | A1 | 7/2012 | Saint-Martin |
| 2014/0135854 | A1 | 5/2014 | Dec et al. |
| 2015/0012046 | A1 | 1/2015 | Saint-Martin |
| 2015/0105827 | A1 | 4/2015 | Martin et al. |
| 2016/0228161 | A1 | 8/2016 | Dec et al. |

FOREIGN PATENT DOCUMENTS

| | | |
|---|---|---|
| JP | 2004183896 A | 7/2004 |
| JP | 2012530550 A | 12/2012 |

OTHER PUBLICATIONS

Japanese Office Action dated Sep. 11, 2018 for corresponding Japanese Patent Application No. 2016-555774.

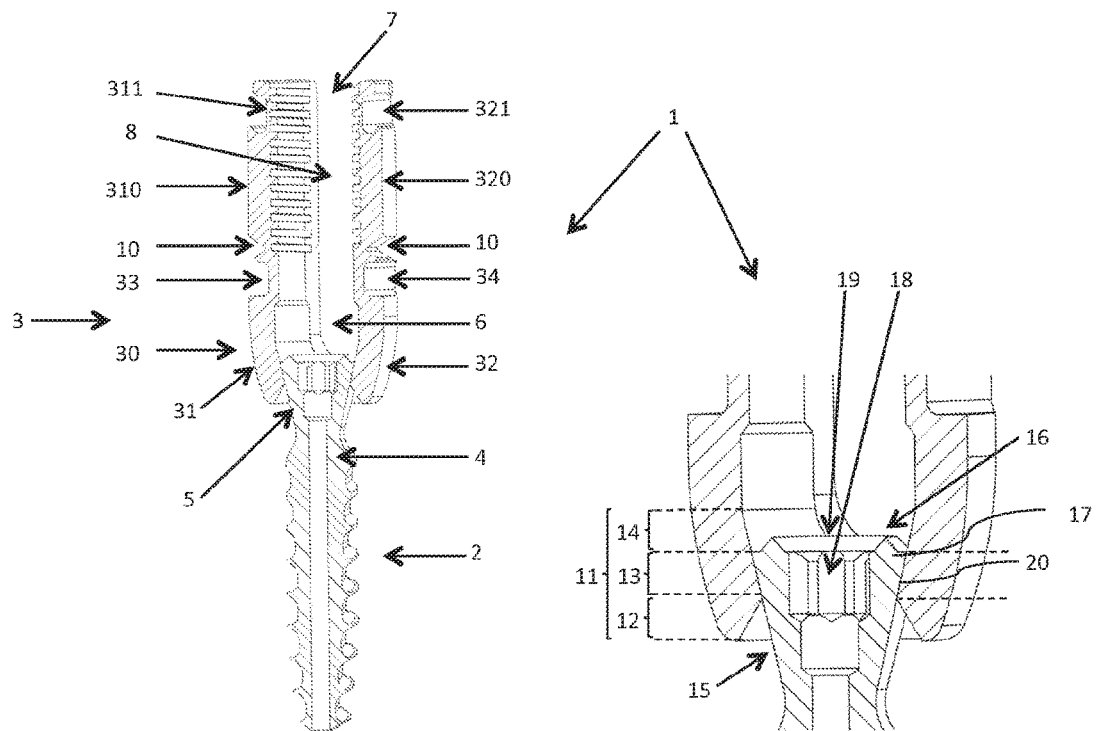
FIG. 1
FIG. 2
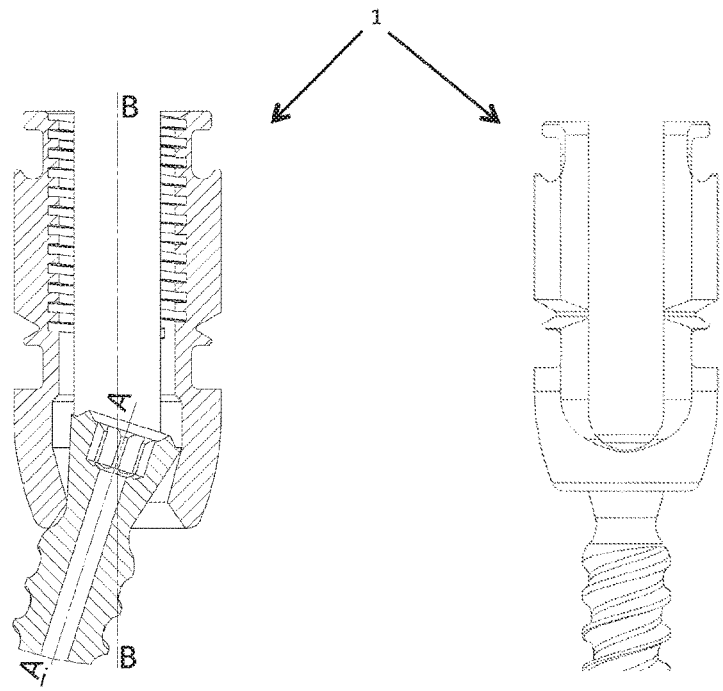
FIG. 3a
FIG. 3b

OSTEOSYNTHESIS SYSTEM COMPRISING MEANS FOR STRAIGHTENING A BONE ANCHORING ELEMENT RELATIVE TO A SCREW HEAD AND ANCHORING SCREW IMPLEMENTED IN SUCH A SYSTEM

BACKGROUND

The invention concerns an osteosynthesis fixation system of a type among those used to treat degenerative or traumatic vertebral deformations, comprising anchoring screws for a vertebra, wherein at least one of the anchoring screws comprises a bone anchoring element provided at one of its ends with a screw head for coupling a connecting element to the bone anchoring element, wherein the bone anchoring element comprises a threaded rod in the vertebra, prolonged at the end by a coupling head for coupling with the screw head, the screw head comprising a body traversed longitudinally by a channel, wherein the channel has, in the lower portion, a receiving cavity for receiving the coupling head of the anchoring element.

The invention also concerns an anchoring screw intended for use with such a system.

The osteosynthesis system and the anchoring screw are intended particularly, but not exclusively, for treatment of major injuries to the vertebral column.

Use of spine stabilisation systems is known for the purpose of bone fusion in order to reduce a dorsolumbar fracture and stabilise the affected region. In the conventional method in itself, the spine stabilisation systems comprise bone anchoring elements designed to be fixed in the vertebrae involved in osteosynthesis (pedicle screws), connecting rods and means of coupling the connecting rods to these bone anchoring elements. Each bone anchoring element is coupled respectively to the connecting rod either by means of a connector, or directly. In the latter case, the bone anchoring element advantageously features a head arranged in order to receive the connecting rod. Conventionally, it is customary to resort to fixed-head anchoring elements in order to control reduction of the vertebrae.

Reduction of the fracture or straightening of the vertebrae is performed first of all by fixing the bone anchoring elements in the vertebrae involved in osteosynthesis and subsequently installing the connecting rod on the head of the bone anchoring element. The anchoring elements are fixed so as to extend appreciably perpendicularly in relation to the vertebra on which they are fixed, whilst the connecting rod must be positioned appreciably parallel to the vertebral column. A tightening nut is subsequently placed on each head, immobilising the connecting rod while allowing a rotational and translational movement of the latter on the head so as to allow performance of the reduction manipulations before final tightening of the nut and thus complete immobilisation of the connecting rod on the head. Straightening of the vertebra is performed gradually, by exerting traction, compression and/or expansion movements on each of the bone anchoring elements implanted on the vertebrae to be straightened with the aid of suitable instruments.

Mounting the connecting rod on the heads of bone anchoring elements often however proves troublesome.

Indeed, installing the connecting rods is the major disadvantage encountered with fixed-head anchoring elements. Depending on the position of the vertebrae, the heads of each bone anchoring element may display different inclinations and directions such that it proves difficult to place a connecting rod on all the heads of the bone anchoring elements. It is necessary in this case to adapt the connecting rods by means of appropriate curvatures. The more severe the deformation of the vertebral column, the more difficult installation of the connecting rods becomes. Moreover, the technique used does not systematically guarantee correct straightening of the vertebrae. Satisfactory straightening is all the more difficult when the curvature of the connecting rod is needed to be modified in order to allow installation of the rod on the heads of the bone anchoring elements.

In order to eliminate this disadvantage encountered with fixed-head anchoring elements, a number of surgeons resort to multiaxial-head anchoring elements. In a manner known per se, these elements comprise a head designed to receive a connecting rod, wherein the head is coupled to an end forming a ball-and-socket joint of a threaded rod. These bone anchoring elements offer the advantage of facilitating installation of the connecting rod on all the receiving heads, whereby the latter may be suitably oriented in order to receive the connecting rod. The disadvantage however of these multiaxial-head anchoring elements is that they cannot serve as a lever to straighten the vertebrae, as is the case with fixed-head anchoring elements, with the screw head of these elements not being completely immobilised on the threaded rod when the tightening nut is installed on the screw head in a tightening position allowing movement of the connecting rod. It is therefore necessary, once the bone anchoring elements, the connecting rod and the tightening nuts are in place, to proceed to reduce the vertebrae either by the method of positioning the patient or by techniques involving bending the connecting rod. These methods prove time-consuming and difficult however and do not ensure straightening of the threaded rod and hence of the vertebra in the axis of the screw head.

The invention aims to solve these problems by proposing an osteosynthesis system and an anchoring screw capable of being used with the osteosynthesis system allowing easier positioning of the connecting rods on the heads of the bone anchoring elements while retaining the functionality of the fixed-head anchoring elements (allowing straightening of the vertebrae).

The purpose of the invention is also to propose an osteosynthesis system and an anchoring screw allowing easier straightening and ensuring correct straightening.

The purpose of the invention is likewise to offer an anchoring screw of small dimensions.

SUMMARY

To this end and according to a first aspect, the invention concerns an anchoring screw designed to be implanted in a vertebra comprising a bone anchoring element provided at one of its ends with a screw head for coupling a connecting element to the bone anchoring element, wherein the bone anchoring element comprises a threaded rod for anchoring in the vertebra, prolonged at the end by a coupling head for coupling with the screw head, the screw head comprising a body traversed longitudinally by a channel, wherein the channel has, in the lower portion, a receiving cavity for receiving the coupling head of the anchoring element, characterised in that the receiving cavity comprises a first area of increasing cross-section towards the bone anchoring element emerging at the bottom end of the screw head, a second area of decreasing cross-section towards the anchoring element, wherein the second area, arranged above the first area, features an opening communicating with the first area of a cross-section larger than the external nominal cross-section of the threaded rod of the bone anchoring element and of smaller cross-section than an external cross-section of the coupling head and a third area communicating with the second area and arranged with the latter to allow the displacement of the screw head on the coupling head and in that the coupling head of the bone anchoring element comprises a contact portion having an outer surface of a shape matching the inside surface of the second area of the receiving cavity.

Owing to the shape of the coupling head of the bone anchoring element and of the cavity receiving the coupling head of the screw head, the latter is able to change from a state in which it is mobile on a bone anchoring element (play allowed between the screw head and the bone anchoring element) to a state in which it is fixed, whereby change from the mobile state to the fixed state is effected by straightening the bone anchoring element until the latter is positioned in alignment with the screw head, with straightening of the bone anchoring element for its part resulting in straightening of the vertebra in which it is to be implanted. Straightening the bone anchoring element implies positioning the bone anchoring element such that its axis is appreciably arranged in the axis of the screw head. In other words, the bone anchoring element is aligned with the screw head.

Advantageously, the second area is truncated cone-shaped.

Advantageously, the first area is truncated cone-shaped.

According to a particular embodiment, the third area comprises a portion of wall, the circular cross-section of which is greater than or equal to the cross-section of the top end of the second area.

Advantageously, provision may be made for the third area's having a larger internal cross-section in relation to the portion of wall with a circular cross-section. This thus provides greater possibilities for displacement of the coupling head within the screw head body.

Advantageously, the coupling head comprises a centering portion, the cross-section of which is appreciably equal to the portion of wall of the third area.

Advantageously, the third area comprises a truncated cone-shaped portion of wall communicating with the second area, wherein the bottom end of the portion of wall has a cross-section greater than or equal to the cross-section of the top end of the second area.

Advantageously, the coupling head comprises a truncated cone-shaped end portion expanding towards the threaded rod.

According to a particular configuration, the coupling head features an upper surface provided with an annular lug for retaining the connecting element. The presence of a lug holds the connecting element in place when the latter is in position in the screw head, thereby avoiding any movement of the element in the body.

According to another configuration, the coupling head features a flat upper surface extending appreciably perpendicularly in relation to the threaded rod.

According to a particular embodiment, the second and third areas form a displacement chamber for the coupling head.

The invention also concerns an osteosynthesis system comprising an anchoring screw as defined above, wherein the bone anchoring element and the screw head body respectively define a longitudinal angle AA and BB, in addition to means of straightening the bone anchoring element in relation to the screw head. The means of straightening are such that they allow the threaded rod of the bone anchoring element to be straightened and placed in the same direction as that of the axis of the screw body.

According to a specific configuration, the means of straightening comprise a tightening nut. Thus, by a single action of screwing the tightening nut onto the screw head, the threaded rod is straightened in relation to the screw head and hence the vertebra on which the anchoring screw is implanted is straightened.

Provision may also be made for the means of straightening comprising a cradle designed to receive the connecting rod, wherein the cradle features a flat lower end surface.

The invention also concerns an osteosynthesis system comprising anchoring screws designed to be implanted respectively in a vertebra, wherein at least one of the anchoring screws comprises a bone anchoring element with a longitudinal axis AA, comprising a threaded anchoring rod prolonged at the end by a coupling head and a screw head for coupling a connecting element to the bone anchoring element, wherein the screw head, installed mobile on the bone anchoring element, comprises a body with a longitudinal axis BB traversed longitudinally by a channel, the lower portion of which has a receiving cavity for receiving the coupling head of the anchoring element, at least one connecting element designed to interconnect the anchoring screws and means of tightening the connecting element on each anchoring screw, wherein the system is remarkable in that the osteosynthesis system comprises means of straightening the bone anchoring element in relation to the screw head (during tightening of the connecting element on the anchoring screw, wherein the means of straightening are arranged so as to straighten the threaded rod of the bone anchoring element and place the former in the longitudinal axis BB of the screw head body.

The expression "place in the longitudinal axis BB of the screw head body" means placing the threaded rod in such a way that the longitudinal axis AA of the anchoring element is merged with the screw head axis.

Advantageously, the means of straightening comprise a cradle designed to receive the connecting element, wherein the cradle has a bottom end of a shape matching the top end of the coupling head.

Advantageously, the bottom end of the cradle is truncated cone-shaped.

Advantageously, the cradle and the coupling head respectively have a flat lower surface and upper end surface.

Advantageously, the receiving cavity arranged in the screw head comprises a first area of increasing cross-section towards the bone anchoring element emerging at the bottom end of the screw head, a second area of decreasing cross-section towards the anchoring element, wherein the second area, arranged above the first area, features an opening communicating with the first area of a cross-section larger than the external nominal cross-section of the threaded rod of the bone anchoring element and of smaller cross-section than an external cross-section of the coupling head and a third area communicating with the second area and arranged with the latter to allow the displacement of the screw head on the coupling head and in that the coupling head of the bone anchoring element comprises a contact portion having an outer surface of a shape matching the inside surface of the second area of the receiving cavity.

Advantageously, the first, second and third areas form, with the contact portion, the means of straightening.

Advantageously, the first and/or second area is(are) truncated cone-shaped.

The invention also concerns an anchoring screw intended for use in an osteosynthesis system as described above. The anchoring screw adopts all the characteristics of the anchoring screw described above.

BRIEF DESCRIPTION OF THE DRAWINGS

Other aims and advantages of the invention will appear in the course of the following description, made with reference to the appended drawings in which:

FIG. 1 illustrates a perspective view in longitudinal cross-section of an anchoring screw according to a first embodiment of the invention;

FIG. 2 illustrates a detailed view of the anchoring screw in FIG. 1;

FIGS. 3a and 3b illustrate front views of the anchoring screw in FIG. 1, in the displacement and tightening positions respectively;

For greater clarity, identical or similar elements of the different embodiments are marked by identical reference signs on all the figures.

Figures 4, 5:
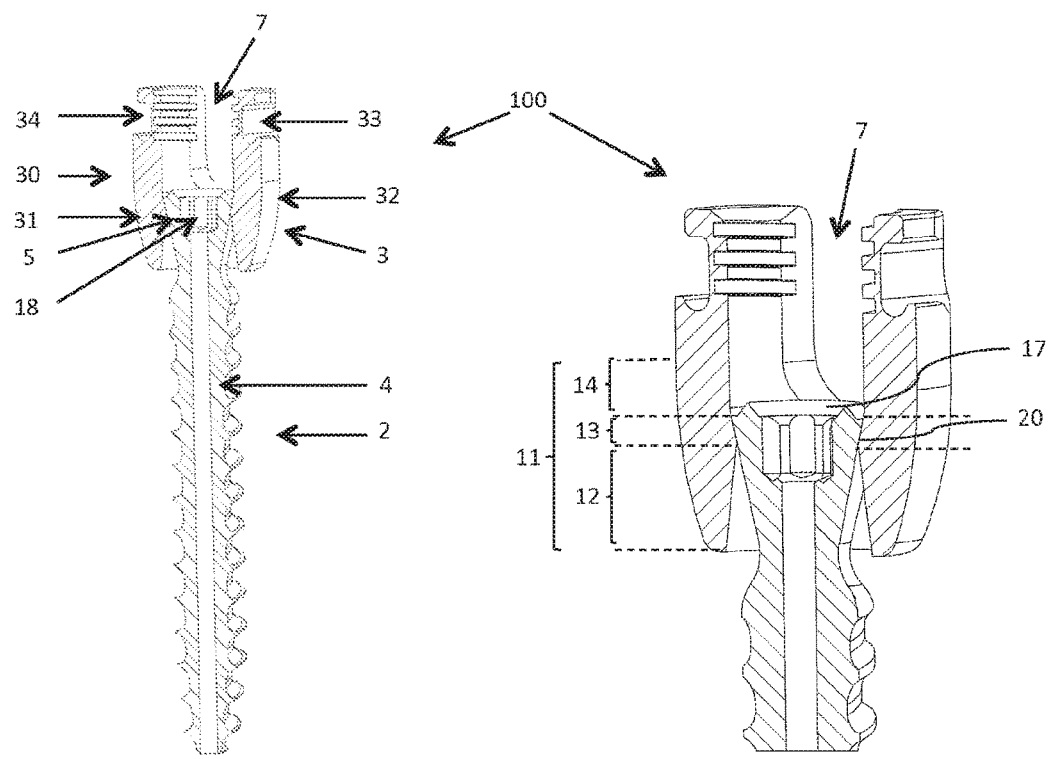
FIG. 4 illustrates a perspective view in longitudinal cross-section of an anchoring screw according to a second embodiment of the invention.
FIG. 5 illustrates a detailed view of the anchoring screw in FIG. 4.
Figures 6A, 6B:
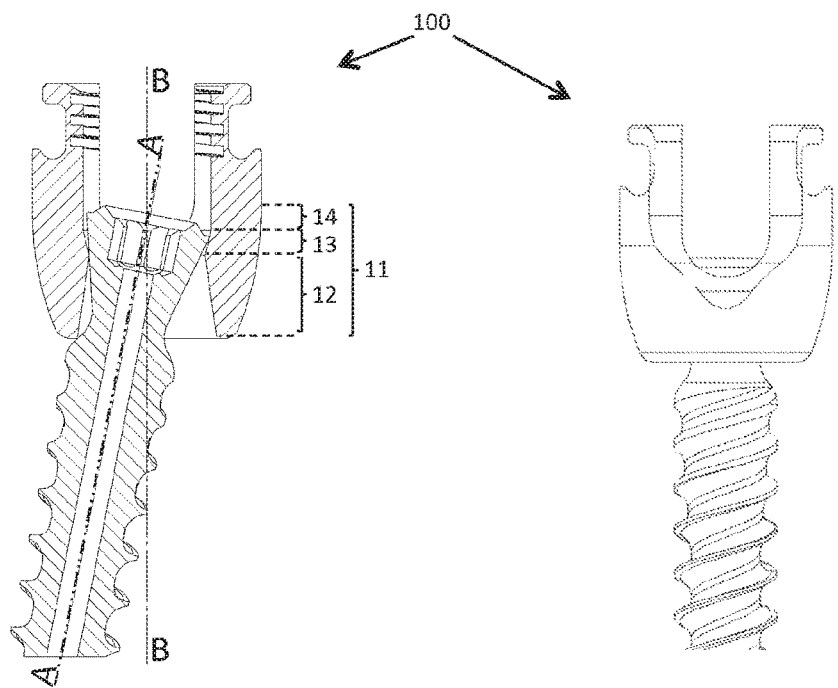
FIGS. 6a and 6b illustrate front views of the anchoring screw in FIG. 4, in the displacement and tightening positions respectively.

Below, the terms "above", "below", "lower" and "upper" are defined with reference to the position of the anchoring screws illustrated in the drawings.

DETAILED DESCRIPTION

In relation with FIGS. 1, 2, 3a and 3b, an anchoring screw 1 is described, designed to be implanted in a vertebra according to a first embodiment.

The anchoring screw comprises a bone anchoring element 2 provided at one of its ends with a screw head 3.

The bone anchoring element 2, with a longitudinal axis AA, comprises a threaded rod 4 designed to be inserted in the vertebra. One of the ends of the threaded rod 4 is provided with a head 5 configured to allow coupling of the threaded rod with the screw head 3. One will subsequently refer to the threaded rod 4 and the coupling head 5 in relation with the threaded rod and the end of the rod providing the coupling with the screw head 3. In the embodiment illustrated, the bone anchoring element 2 is cannulated.

The screw head 3 features, in a manner known per se, a screw head body 30 with a longitudinal axis BB, comprising two lateral arms 31, 32, arranged in order to delimit a U-shaped crossways channel 6 designed to receive a connecting element of the connecting rod type. The screw head body 30 is traversed longitudinally by a channel 7. The axis of the longitudinal channel corresponds to the longitudinal axis BB of the screw head body 30. The screw head body 30 also comprises notches 33, 34 for engagement of a specific instrument, such as a guide tube for example used as part of minimally invasive surgical operations.

In the embodiment illustrated, each of the lateral arms 31, 32 comprises a longitudinal extension 310, 320. The extensions 310, 320 delimit a tapped, traversing, longitudinal cavity 8. They furthermore comprise notches 311, 321, for engagement of a specific instrument, such as a guide tube for example used as part of minimally invasive surgical operations. Each arm 31, 32 is connected to a corresponding extension 310, 320 by a break area 10 allowing removal of the extension once the operation is completed. This possesses the advantage of avoiding leaving unnecessary parts in the body once the surgical operation has been performed. These break areas 10 are formed by notches, the depth and geometry of which are determined in order to achieve a clean break when a lateral force exceeding a threshold value is exerted with a specific instrument on one of the extensions.

A screw head 3 of this kind is intended in particular for treatment of major injuries. It is of course obvious that the anchoring screw 1 according to the invention is not limited to such an application and that the screw head 3 may have a conventional shape (i.e. not comprising any extension) like the heads illustrated in FIGS. 4 to 6a, 6b without departing from the framework of the invention.

The lower portion of the longitudinal channel 7 features a receiving cavity 11 designed to receive the coupling head 5 of the anchoring element 2.

The receiving cavity 11 features a first area 12 of increasing cross-section towards the bone anchoring element 2 and a second area 13 of decreasing cross-section towards the anchoring element, wherein the second area 13 is arranged above the first area 12, communicating with the latter. The first area 12 emerges directly in the second area 13. The communicating opening between the areas advantageously features a cross-section larger than the external nominal cross-section of the threaded rod of the bone anchoring element 2 and a cross-section smaller than an external cross-section of the coupling head 5. Hence, the through opening is dimensioned to allow coupling of the screw head 3 with the bone anchoring element 2 (insertion of the bone anchoring element 2 through the top of the screw head 3). The receiving cavity 11 furthermore comprises a third area 14 communicating with the second area 13 and located above the latter. In the embodiment illustrated, the third area 14, directly communicating with the second area 13, extends in the prolongation of the latter, thereby forming a truncated cone-shaped cavity. The receiving cavity 11 is therefore substantially hourglass-shaped.

As will become clear later, the function of the first area 12 and the second area 14 is to allow displacement of the screw head 3 on the bone anchoring element 2, thereby facilitating positioning of the connecting rod, whilst the function of the second area 13 is to allow straightening of the threaded rod 4 in the longitudinal axis of the longitudinal channel 7 of the screw head 3 and therefore straightening of the vertebra when a means of tightening, of the bolt type, is engaged in the corresponding channel 7. Subsequently, the first area 12 and the third area 14 will be respectively designated adjusting cone 12 (or displacement cone 12) and displacement chamber 14 and the second area 13, tightening cone 13 (or straightening cone 13).

In the embodiment illustrated, the upper part of the hourglass shape formed by the tightening cone 13 and the displacement chamber 14 is of a height at least twice the height of the lower part of the hourglass shape formed by the displacement cone 12. Furthermore, the upper part has a vertex angle in relation to the longitudinal axis BB smaller than the vertex angle of the lower part.

The coupling head 5 of the bone anchoring element 2 has an outside surface 15 of a shape matching the inside surface of the tightening cone 13. More specifically, the coupling head 5 has a substantially truncated cone shape flaring out in the direction opposite to the threaded rod 4, of a conicity similar and preferably identical to the conicity of the tightening cone 13. When the anchoring screw is in the fixed position (i.e. after straightening the anchoring element), the wall of the tightening cone is thus in contact with a portion of the wall of the coupling head. This portion of wall will subsequently be denoted by the expression "contact portion" under the reference 20.

Owing to the hourglass shape of the receiving cavity 11 and the inverted truncated cone shape of the coupling head 5, the anchoring screw 1 jointly functions as a multiaxial screw and a fixed screw. It allows displacement of the screw head 3 on the bone anchoring element 2 and straightening of the bone anchoring element 2 in the axis of the screw head 3 (axis corresponding to the axis of the hourglass shape) when the connecting rod and the tightening nut are placed on the screw head 3.

Advantageously, the anchoring screw 1 comprises a retaining means 16 holding the connecting rod in position when the latter is installed in the corresponding channel 6 of the screw head 3. In the embodiment illustrated, the retaining means 16 come in the form of an annular lug 17 arranged on the upper surface of the coupling head. It is of course obvious that the invention is not limited to this type of retaining means and that provision may be made in particular for several discontinuous lugs.

Advantageously, the coupling head 5 comprises a cavity 18 emerging on the top end 19 and more specifically on the upper surface forming the base of the truncated cone shape of the coupling head 5. The cavity 18 is arranged in order to receive the end of an instrument, such as for example the end of a driving instrument of the screwdriver type.

FIGS. 4, 5, 6a and 6b illustrate an anchoring screw 100 according to another embodiment of the invention. In this second embodiment, the displacement chamber 14 has a circular cross-section and extends in the prolongation of the second area 13 in a direction appreciably parallel to the longitudinal axis BB of the screw head 3. As above, the displacement chamber 14 emerges directly in the tightening cone 13. In order to allow passage of the bone anchoring element 2 through the top of the screw head 3, the displacement chamber 14 and the coupling head 5 are dimensioned so as to allow slight play between the internal wall 36 of the displacement chamber 14 and the larger external diameter of the coupling head 5. Slight play implies play that is sufficient to allow passage of the bone anchoring element into the screw head 3 and displacement of the screw head 3 on the bone anchoring element 2 while ensuring optimum external dimensions of the screw head 3.

Advantageously, the tightening cone 13 features a generator of a length of between 1.5 millimeters and 3 millimeters, preferably approximately 2 millimeters.

In the embodiment illustrated, the upper part of the receiving cavity 11 formed by the tightening cone 13 and the displacement chamber 14 is of a height appreciably equal to the height of the lower part of the receiving cavity 11 formed by the displacement cone 12. The tightening cone 13 for its part has a height smaller than that of the displacement chamber 14. The upper part has a vertex angle in relation to the longitudinal axis BB appreciably similar to that of the lower part. It is of course obvious that this embodiment is not limited to these dimensions and provision may be made for other dimensions according to the desired displacement, the size of the anchoring screw, etc., without departing from the framework of the invention.

Figure 7A:
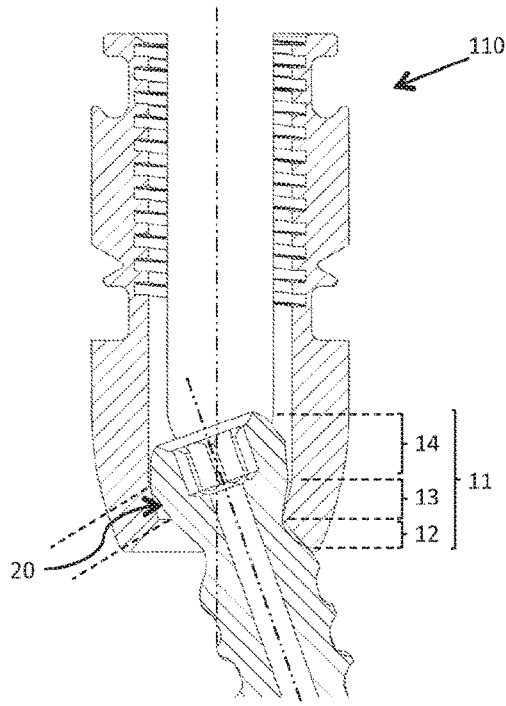
FIGS. 7a and 7b illustrate front views of an embodiment variant of the anchoring screw in FIG. 4, wherein the anchoring screw is shown in the displacement and tightening positions respectively.
Figure 7B:
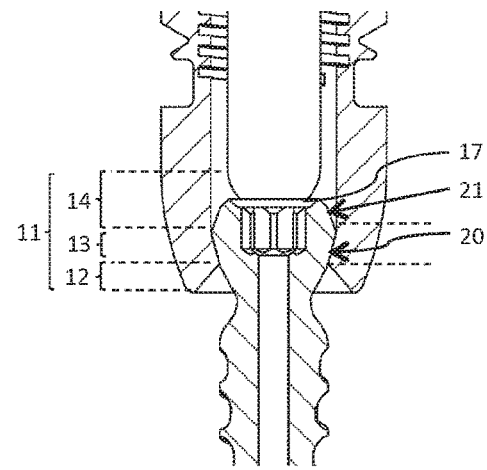

FIGS. 7a and 7b show an embodiment variant of the anchoring screw 100 illustrated in FIGS. 4, 5, 6a and 6b (anchoring screw referenced 110).

In this embodiment, the coupling head 5 comprises a portion displaying a truncated cone shape matching the internal wall of the tightening cone 13 of the screw head 3. This portion of the coupling head 5 thus forms the contact portion 20 designed to be brought into contact with the wall of the tightening cone 13 during straightening of the bone anchoring element 2. The contact portion 20 is advantageously extended by an end portion 21 of an inverted truncated cone shape in relation to that of the contact portion 20. In the embodiment illustrated, the external cross-section of the base of the end portion 21 is equal to the external cross-section of the base of the contact portion 20. The advantage of providing a contact portion 20 extended by a truncated cone-shaped end portion 21 lies in increasing the volume of the coupling head 5 while allowing displacement of the screw head 3 on the coupling head 3. By increasing the volume of the coupling head 5, any break areas present at the level of the cavity 18 and the coupling head when the latter does not have an end portion are eliminated.

Advantageously and as in the embodiments described above, the anchoring screw 110 comprises retaining means for retaining the connecting rod on the screw head 3. In the present case, the retaining means comprise an annular lug arranged on the upper surface (end surface) of the end portion 21. The advantage of the inverted truncated cone shape of the end portion 21 lies in not restricting the movement of the screw head 3 on the coupling head 5 of the bone anchoring element 2.

The displacement chamber 14, as in the embodiment described above, displays a circular cross-section and extends appreciably parallel to the longitudinal axis of the screw head 3.

In the embodiment illustrated, the height of the tightening cone 13 is appreciably equal to the height of the displacement cone 12. It furthermore has a vertex angle in relation to the longitudinal axis BB smaller than that of the displacement cone 12. It is of course obvious that this embodiment is not limited to these dimensions and provision may be made for other dimensions according to the desired displacement, the size of the anchoring screw, etc., without departing from the framework of the invention.

Furthermore, the screw head 3 illustrated is a head arranged for treatment of major injuries (similar configuration of the screw head of the anchoring screw in FIG. 1). It is of course obvious that the screw head 3 may have a conventional shape, as illustrated in FIG. 4.

Figure 8A:
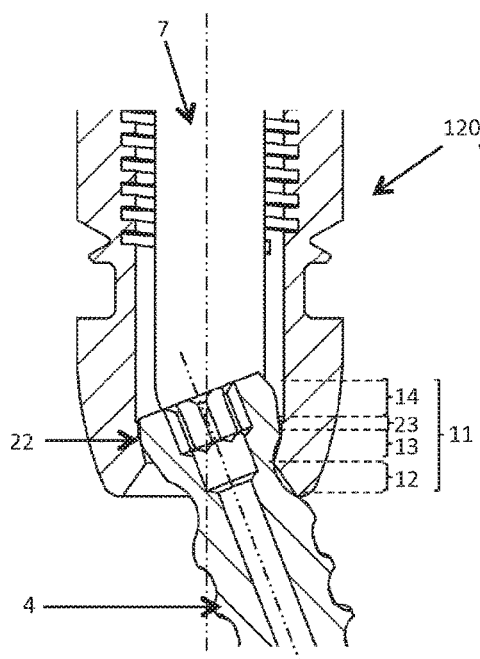
FIGS. 8a and 8b illustrate views in longitudinal cross-section of an anchoring screw according to another embodiment, wherein the anchoring screw is shown in the displacement and tightening positions respectively.
Figure 8B:
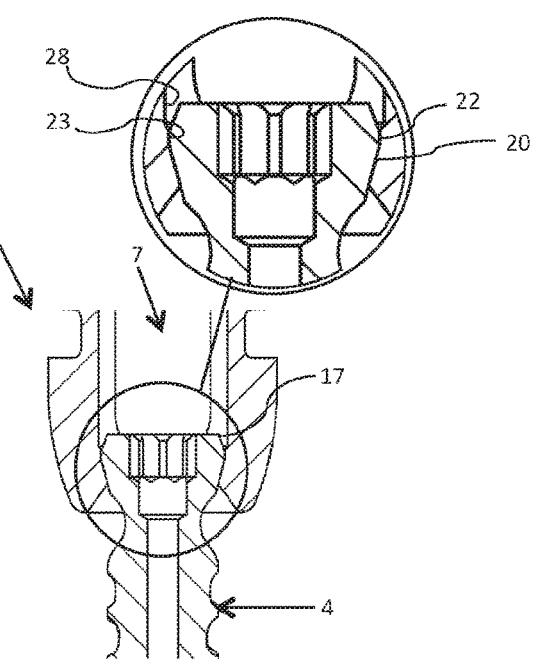

FIGS. 8a and 8b illustrate an anchoring screw 120 according to another embodiment.

In this embodiment, the displacement chamber 14, as in the embodiment described above, displays a circular cross-section 23 and extends appreciably parallel to the longitudinal axis of the screw head 3. It communicates however with the tightening cone 13 by means of a centering area. The centering area 23, circular in cross-section, extends appreciably in the longitudinal axis BB of the screw head 3. The centering area 23 is intended to be brought into position opposite a circular portion of the coupling head 5, known as the centering portion 22, during the straightening operation. In the embodiment described, retaining means are arranged on the upper surface of the centering portion 22. The centering portion of the coupling head 5 and the centering area of the screw head 3 thus allow alignment of the threaded rod 4 in relation to the longitudinal channel 7 of the screw head 3. In order to allow displacement of the coupling head 5, the displacement chamber 14 has an internal cross-section larger than the internal cross-section of the centering area 23. This change in cross-section is denoted by the reference 28. The displacement position is subsequently obtained by slightly sliding the screw head 3 on the threaded rod 4 towards the anchoring end of the latter.

Although not illustrated, provision may be made for the coupling head's 5 also comprising an end portion of an inverted truncated cone shape in relation to that of the contact portion 20 similar to the end portion 21 of the coupling head 5 illustrated in FIGS. 7a and 7b.

Figure 9A:
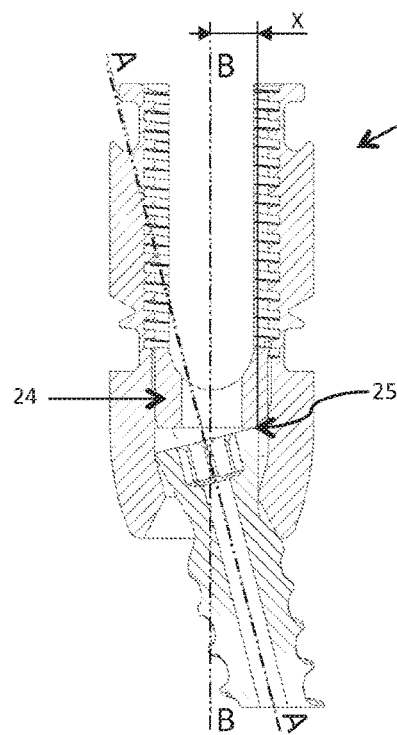
FIGS. 9a and 9b illustrate views in longitudinal cross-section of an anchoring screw according to another embodiment, wherein the anchoring screw is shown with a cradle, in the displacement position and fixed position respectively.
Figure 9B:
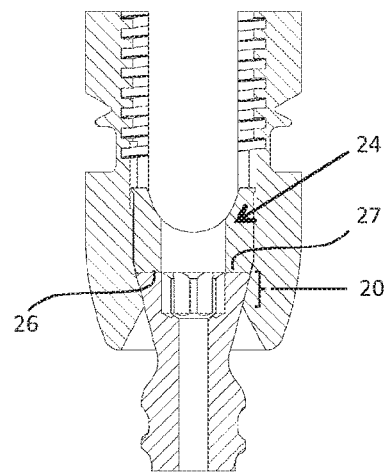
Figure 11:
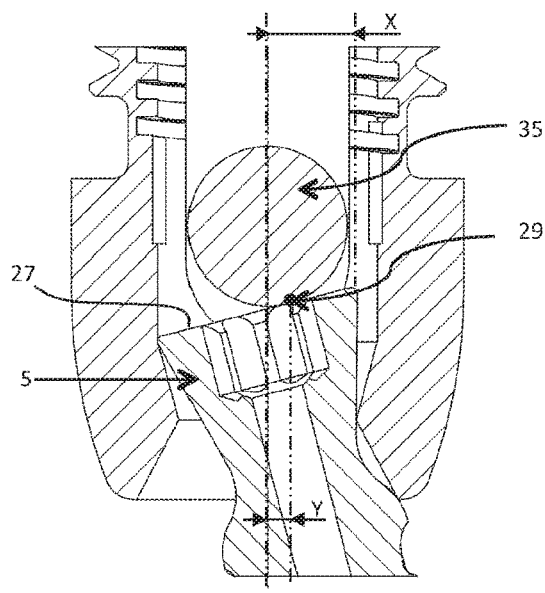
FIG. 11 shows a view of the coupling head illustrated in FIG. 9A in contact with a connecting rod.

In the embodiments described above, straightening of the bone anchoring element 2 is performed by the connecting rod when installing the tightening nut in the screw head 3. According to these configurations, the presence of a cradle between the coupling head 5 and the connecting rod is not required. One may of course consider making provision for using the anchoring screws described above with a cradle 24 having a flat lower contact surface 26 without departing from the context of the invention, as illustrated in FIGS. 9a and 9b. It is clear in this case that the coupling head 5 will have a preferably flat end surface 27. The advantage of using a cradle having a flat lower contact surface and a coupling head 5 with a flat end surface lies in offering optimum leverage regardless of the implantation axis of the anchoring rod 4 in the vertebra. Indeed, as illustrated in FIG. 9a, the contact point 25 between the cradle 24 and the coupling head 5 when the screw head 3 is inclined in relation to the bone anchoring element 2 is located on the edge of the top end of the coupling head 5. A contact point of this kind cannot be obtained with a connecting rod. Indeed, as shown in FIG. 11, the contact point 29 obtained with a connecting rod 35 has a distance Y in relation to the longitudinal axis BB less than the distance X obtained with the cradle.

Figure 10A:
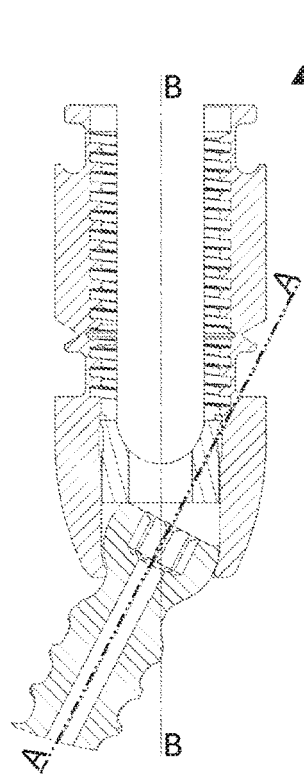
FIGS. 10a and 10b illustrate views in longitudinal cross-section of an anchoring screw according to another embodiment, wherein the anchoring screw is shown with a cradle, in the displacement position and fixed position respectively.
Figure 10B:
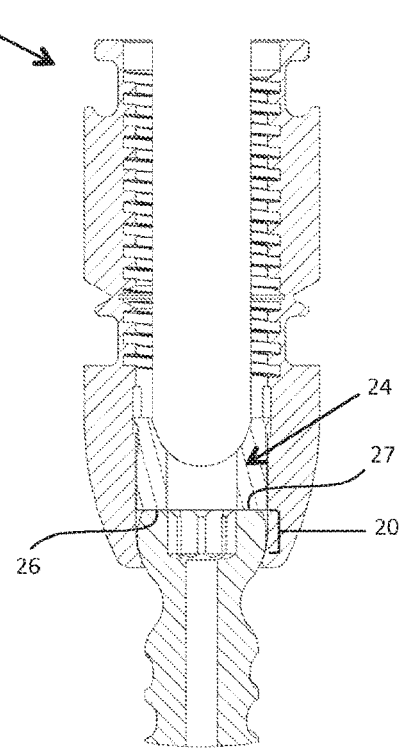

Use of a cradle 24 may however prove necessary depending on the shape of the coupling head 5. An example of such a configuration is illustrated in FIGS. 10a and 10b. In this embodiment, in addition to the truncated cone-shaped contact portion 20, the coupling head 5 is formed of several truncated cone-shaped portions. These truncated cone-shaped portions are arranged in relation to each other so as to give the coupling head 5 a shape similar to that of a hemisphere. The screw head in this case is installed mobile in rotation on the bone anchoring element 2. The presence of a cradle 24 as described above is required here, in combination with the connecting rod and the tightening nut, in order to lock completely the rotational movement of the screw head 3 and intervene in straightening the bone anchoring element 2 in the axis of the screw head during straightening of the vertebra.

Figures 12A, 12B:
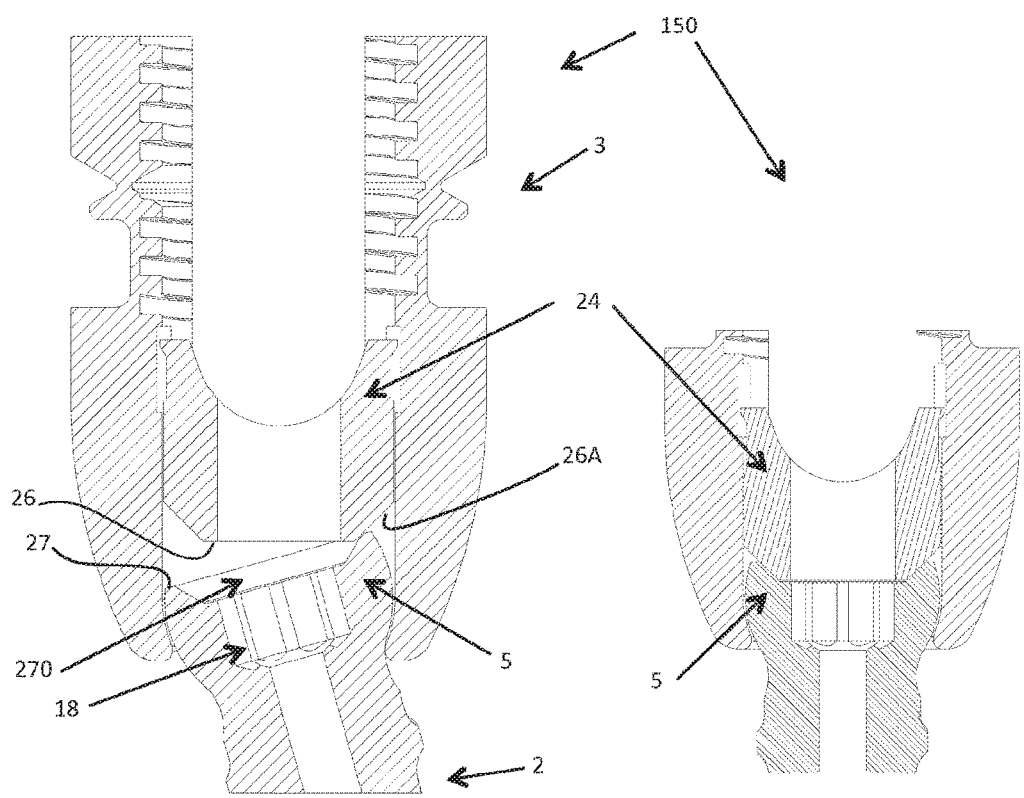
FIGS. 12a and 12b illustrate views in longitudinal cross-section of an anchoring screw according to another embodiment, wherein the anchoring screw is shown with a cradle, in the displacement position and fixed position respectively.

FIGS. 12a and 12b illustrate another embodiment of an anchoring screw 150 equipped with a cradle 24, wherein the anchoring screw is shown in the displacement position and fixed position respectively. In this embodiment, the elements (screw head 3, bone anchoring element 2 and cradle 24) essentially adopt the structure of those described in relation with FIGS. 10a and 10b. The cradle 24 and the coupling head 5 of the anchoring element 2 differ however by the configuration of the contact areas employed by the cradle and the coupling head. In this embodiment, the cradle 24 comprises a chamfered end surface 26 (chamfer 26 A). The cradle 24 thus has a truncated cone-shaped bottom end portion. The coupling head, for its part, has an upper end surface 27 provided with a truncated cone-shaped bore 270 matching that of the end portion of the cradle 24. As illustrated in FIG. 12b, the bore 270 is dimensioned and arranged such that the coupling head 5 interacts with the end portion of the cradle 26 when the bone anchoring element 2 is positioned extending in the axis of the screw head 3. The bore 270 emerges in the cavity 18 for receiving the end of the instrument.

When screwing the tightening bolt in the screw head 3, the chamfered area 26 A of the cradle 24, under the pushing action of the connecting rod, comes into contact with the upper border of the bore (border delimited by the surface 27 and the bore 270). The advantage of this configuration lies in improving distribution of the stresses and thus reducing the frictions between the cradle 24 and the coupling head 5.

In order to enhance reduction of friction, provision may also be made for submitting the cradle and bone anchoring element to a chemical treatment, such as anodization for example.

According to an embodiment variant, provision may be made for a reverse configuration for the contact surface of the cradle and the coupling head. Hence, provision may be made for the coupling head's having a truncated cone-shaped top end portion, wherein the conicity decreases in the direction opposite to the threaded anchoring rod, while the cradle features an end surface provided with a bore of a shape matching the truncated cone-shaped end portion of the coupling head when the bone anchoring element is positioned in the axis of the screw head.

The invention is described above by way of an example. It is understood that the person skilled in the art is capable of producing different variants of embodiment of the invention without departing from the framework of the invention.

The invention claimed is:

1. An osteosynthesis system comprising:
   anchoring screws designed to be implanted respectively in a vertebra, wherein at least one of the anchoring screws comprises a bone anchoring element with a longitudinal axis (AA), comprising a threaded anchoring rod prolonged at the end by a coupling head and a screw head for coupling a connecting element to the bone anchoring element, wherein the screw head, installed mobile on the bone anchoring element, comprises a body with a longitudinal axis (BB) traversed longitudinally by a channel featuring in the lower portion a receiving cavity for receiving the coupling head of the anchoring element,
   at least one connecting element designed to interconnect the anchoring screws,
   means of tightening the connecting element on each anchoring screw, wherein the osteosynthesis system comprises means of straightening the bone anchoring element in relation to the screw head during tightening the connecting element on the anchoring screw, wherein the means of straightening are arranged so as to straighten the threaded rod of the bone anchoring element and place the former in the longitudinal axis (BB) of the screw head body.

2. The system according to claim 1, wherein the means of straightening comprise a cradle designed to receive the connecting element, wherein the cradle has a bottom end of a shape matching the top end of the coupling head.

3. The osteosynthesis system according to claim 2, wherein the bottom end of the cradle is truncated cone-shaped.

4. The osteosynthesis system according to claim 2, wherein the cradle and the coupling head respectively have a flat lower surface and upper end surface.

5. The osteosynthesis system according to claim 1, wherein the receiving cavity arranged in the screw head comprises a first area of increasing cross-section towards the bone anchoring element emerging at the bottom end of the screw head, a second area of decreasing cross-section towards the anchoring element, wherein the second area, arranged above the first area, comprises an opening communicating with the first area of a cross-section larger than the external nominal cross-section of the threaded rod of the bone anchoring element and of smaller cross-section than an external cross-section of the coupling head and a third area communicating with the second area and arranged with the latter to allow the displacement of the screw head on the coupling head and in that the coupling head of the bone anchoring element comprises a contact portion having an outer surface of a shape matching the inside surface of the second area of the receiving cavity.

6. The osteosynthesis according to claim 5, wherein the first, second and third areas form, with the contact portion, the means of straightening.

7. The osteosynthesis system according to claim 6, wherein at least one of the first and/or second area is truncated cone-shaped.

8. An anchoring screw designed to be used in an osteosynthesis system according to claim 1, comprising a bone anchoring element provided at one of an anchoring screw ends with a screw head for coupling a connecting element to the bone anchoring element, wherein the bone anchoring element comprises a threaded rod for anchoring in the vertebra, prolonged at the end by a coupling head for coupling with the screw head, the screw head comprising a body traversed longitudinally by a channel, wherein the channel has, in the lower portion, a receiving cavity for receiving the coupling head of the anchoring element, wherein the receiving cavity comprises a first area of increasing cross-section towards the bone anchoring element emerging at the bottom end of the screw head, a second area of decreasing cross-section towards the anchoring element, wherein the second area, arranged above the first area, features an opening communicating with the first area of a cross-section larger than the external nominal cross-section of the threaded rod of the bone anchoring element and of smaller cross-section than an external cross-section of the coupling head and a third area communicating with the second area and arranged with the latter to allow the displacement of the screw head on the coupling head and in that the coupling head of the bone anchoring element comprises a contact portion having an outer surface of a shape matching the inside surface of the second area of the receiving cavity.

9. The anchoring screw according to claim 8, wherein the second area is truncated cone-shaped.

10. The anchoring screw according to claim 9, wherein the first area is a truncated cone-shaped.

11. The anchoring screw according to claim 10, wherein the third area comprises a portion of wall, the circular cross-section of which is greater than or equal to the cross-section of the top end of the second area.

12. The anchoring screw according to claim 11, wherein the third area has a larger internal cross-section in relation to the portion of wall with a circular cross-section.

13. The anchoring screw according to claim 12, wherein the coupling head comprises a centering portion, the cross-section of which is appreciably equal to the portion of wall of the third area.

14. The anchoring screw according to claim 13, wherein the third area comprises a truncated cone-shaped portion of wall communicating with the second area, wherein the bottom end of the portion of wall has a cross-section greater than or equal to the cross-section of the top end of the second area.

15. The anchoring screw according to claim 14, wherein the coupling head comprises a truncated cone-shaped end portion expanding towards the threaded rod.

16. The anchoring screw according to claim 15, wherein the coupling head features an upper surface provided with an annular lug for retaining the connecting element.

17. The anchoring screw according to claim 15, wherein the coupling head features a flat upper surface extending appreciably perpendicularly in relation to the threaded rod.

18. The anchoring screw according to claim 10, wherein the second and third areas form a displacement chamber of the coupling head.

* * * * *